(12) United States Patent
Schramm

(10) Patent No.: US 8,361,995 B2
(45) Date of Patent: Jan. 29, 2013

(54) DRUG COMPRISING AT LEAST ONE GESTAGEN

(75) Inventor: Georg Schramm, Stolberg (DE)

(73) Assignee: Richter Gedeon Nyrt., Budapest (HU)

( * ) Notice: Subject to any disclaimer, the term of this patent is extended or adjusted under 35 U.S.C. 154(b) by 714 days.

(21) Appl. No.: 12/553,682

(22) Filed: Sep. 3, 2009

(65) Prior Publication Data

US 2010/0063014 A1 Mar. 11, 2010

Related U.S. Application Data

(63) Continuation of application No. PCT/EP2008/001532, filed on Feb. 27, 2008.

(30) Foreign Application Priority Data

Mar. 7, 2007 (DE) .......................... 10 2007 011 486

(51) Int. Cl.
*A61K 31/56* (2006.01)
(52) U.S. Cl. ....................................................... 514/170
(58) Field of Classification Search .................... 514/170
See application file for complete search history.

(56) References Cited

U.S. PATENT DOCUMENTS 4,171,358 A 10/1979 Black

FOREIGN PATENT DOCUMENTS

| DE | 1568062 A1 | 2/1970 |
| DE | 4339934 A1 | 11/1994 |
| DE | 19739916 A1 | 3/1999 |
| WO | 00/38691 A | 7/2000 |
| WO | 02/22110 A | 3/2002 |
| WO | 2006/013464 A | 2/2006 |
| WO | 2007/002862 A | 1/2007 |
| WO | 2007/085420 A | 8/2007 |
| WO | 2007/098828 A | 9/2007 |

OTHER PUBLICATIONS

Resnik, JAMA, 1967;199(9):601-605.*
Bundesverband Der Pharmazeutischen Industrie E V Und Weitere ED—Rote Liste Service GMBH (ED): "Rote Liste 2002, passage" Rote Liste 2002. Arzneimittelverzeichnis Fuer Deutschland (Einschlieslich EU—Zulassungen Und Bestimmter Medizinprodukte); [Rote Liste], Aulendorf : Editio Cantor, DE, Jan. 1, 2002.
Anonym: "Chlormadinon 2 mg Jenapharm Tbl" Gelbe Liste Pharmindex, XX, XX, Jan. 1, 2006.
Honma S et al: "Identification and Anti—Androgenic Activity of the Metabolites of 17Alpha-Acetoxy-6-Chloropregna-4,6-Diene-3,20-Diene (Chlormadinone Acetate) in the Rat, Rabbit, Dog an Dman" Chemical and Pharmaceutical Bulletin, Pharmaceutical Society of Japan, Tokyo, Bd. 25, Nr. 8, Aug. 25, 1977, pp. 2019-2031.
English Language Abstract for DE 19739916.
English Language Abstract for DE 4339934.
English Language Abstract for WO 2007/085420.
English Language Abstract for WO 2007/098828.

* cited by examiner

*Primary Examiner* — San-Ming Hui
(74) *Attorney, Agent, or Firm* — Jason D. Voight

(57) ABSTRACT

The present invention relates to the use of at least one gestagen selected from the group consisting of chlormadinone acetate, 3α-hydroxy-6-chloro-17α-acetoxy-4,6-pregnadien-20-one (3α-hydroxy-chlormadinone acetate) and 3β-hydroxy-6-chloro-17α-acetoxy-4,6-pregnadien-20-one (3β-hydroxy-chlormadinone acetate) as gestagen component and optionally at least one oestrogen selected from the group consisting of ethinyl oestradiol, oestrone, oestriol as oestrogen component and oestradiol to produce a medicament for the treatment and/or prevention of melasma and optionally for simultaneous hormonal contraception or optionally for simultaneous hormone replacement for women.

21 Claims, No Drawings

DRUG COMPRISING AT LEAST ONE GESTAGEN

This application is a Continuation of 371 application of PCT/EP2008/001532 filed Feb. 27, 2008, which claims priority to the German application 10 2007 011 486.0 filed Mar. 7, 2007.

The present invention relates to the use of at least one gestagen selected from the group consisting of chlormadinone acetate, 3α-hydroxy-6-chloro-17α-acetoxy-4,6-pregnadien-20-one (3α-hydroxy-chlormadinone acetate) and 3β-hydroxy-6-chloro-17α-acetoxy-4,6-pregnadien-20-one (3β-hydroxy-chlormadinone acetate) and optionally at least one oestrogen selected from the group consisting of ethinyl oestradiol, oestrone, oestriol and oestradiol to produce a medicament for the treatment and/or prevention of melasma and optionally for simultaneous hormonal contraception or optionally for simultaneous hormone replacement for women.

A very frequent side-effect which may be observed when taking hormone preparations, in particular when taking contraceptives, is hyperpigmentation of the facial skin in the form of brownish-grey pigmentation marks, often in the form of contiguous blotches, which is also known as Melasma (previously Chloasma). An elevated oestrogen level is responsible for this hyperpigmentation.

Such hyperpigmentation of the facial skin is a major problem, since the skin blotches are regarded as extremely troublesome and the quality of life of those affected is sometimes severely impaired thereby.

To make matters worse, treatment of this pigment disturbance is lengthy and often not very satisfactory. So far, no active therapeutic agents are known for treating melasma.

There is therefore a need for a medicament to be made available which is suitable for the treatment and/or prevention of melasma and optionally for simultaneous hormonal contraception or optionally for simultaneous hormone replacement above all during the peri- or postmenopausal phases.

This object is achieved by the use of at least one gestagen selected from the group consisting of chlormadinone acetate, 3α-hydroxy-6-chloro-17α-acetoxy-4,6-pregnadien-20-one (3α-hydroxy-chlormadinone acetate) and 3β-hydroxy-6-chloro-17α-acetoxy-4,6-pregnadien-20-one (3β-hydroxy-chlormadinone acetate) and optionally at least one oestrogen selected from the group consisting of ethinyl oestradiol, oestrone, oestriol and oestradiol to produce a medicament for the treatment and/or prevention of melasma and optionally for simultaneous hormonal contraception or optionally for simultaneous hormone replacement in women.

The medicament is preferably provided in the form of daily units, which are preferably formulated in the form of tablets. Preferably, the hormone-containing daily units contain as their gestagen component in each case only at least one of the stated gestagens.

For the treatment or prevention of melasma, the daily units preferably in each case contain, as their hormonal active substance, at least one of the above-stated gestagens in a quantity of preferably 10 mg, particularly preferably 2 to 5 mg and very particularly preferably 2.5 to 4 mg.

In addition, the above-stated gestagens may be used in any desired mixing ratio.

In a preferred embodiment of the present invention the gestagen component used according to the invention is one of the following components a) to e), preferably as the sole hormone component of the medicament according to the invention a) chlormadinone acetate,
b) 3α-hydroxy-chlormadinone acetate,
c) 3β-hydroxy-chlormadinone acetate,
d) a mixture of b) and c) in any desired mixing ratio,
e) a mixture of a), b) and/or c) in a mixing ratio of 10 to 90 wt. % chlormadinone acetate and 90 to 10 wt. %, relative to the total mixture, of the other gestagens.

If women are also to be provided at the same time with satisfactory contraceptive protection and at least one of the above-stated gestagens is used as the sole gestagen component or sole hormone component, 1, 2, 3, 4 or 5 mg of chlormadinone acetate, 3α-hydroxy-chlormadinone acetate and/or 3β-hydroxy-chlormadinone acetate and optionally conventional auxiliary materials are preferably used to produce a daily unit.

If, in addition to the treatment of melasma, hormone replacement therapy is also carried out at the same time, the hormone-containing daily units in each case contain at least one of the above-stated gestagens as the sole hormone component, preferably 1, 2, 3, 4 or 5 mg of chlormadinone acetate, 3α-hydroxy-chlormadinone acetate and/or 3β-hydroxy-chlormadinone acetate and optionally conventional auxiliary materials.

Particularly preferably, chlormadinone acetate is used as the preferably sole hormonal active substance for the treatment and/or prevention of melasma and optionally for simultaneous hormonal contraception or optionally for simultaneous hormone replacement.

The number of daily units of a medicament which contains only at least one of the above-stated gestagens as the sole hormone component may correspond at least to a natural female monthly menstrual cycle. To this end, the medicament is preferably provided in the form of at least 28 daily units containing at least one of the stated gestagens as hormonal active substance for uninterrupted daily oral administration. It is also possible, however, for the total number of daily units containing this hormonal active substance to be greater than that corresponding to a natural, female monthly cycle, so making possible preferably uninterrupted intake of the medicament for up to two years, preferably up to 1 year, for the treatment of melasma and optionally for simultaneous hormonal contraception or optionally for simultaneous hormone replacement.

In a preferred embodiment of the present invention the medicament, which contains at least one of the above-stated gestagens as the preferably sole hormone component, is provided in the form of 28, 56, 84, 112, 140, 168, 196, 224, 252, 280, 308, 336 or 364 daily units for uninterrupted daily oral administration.

The medicament according to the invention, which contains as the preferably sole hormone component at least one of the above-stated gestagens, may also be a constituent of a kit, such a kit preferably comprising at least 28 daily units corresponding to the female menstrual cycle of 28 days, these preferably being packaged together in a blister pack and preferably with an indication of the daily unit to be taken in each case. 1, 2, 3, 4, 5, 6, 7, 8, 9, 10, 11, 12, 13, 14 or 15 blister packs in each case comprising 28 daily units, which contain as hormone component in each case at least one of the above-stated gestagens preferably as the sole hormone component, may however also be contained in a kit. The kit optionally also includes a calendar or a diary.

Preferably, the gestagen-containing daily units in each case contain the same quantity of at least one of the stated gestagens.

In a further preferred embodiment, the medicament for the treatment and/or prevention of melasma and optionally for simultaneous hormonal contraception or optionally for simultaneous hormone replacement contains a hormonal active substance combination consisting of at least one gestagen selected from the group consisting of chlormadinone acetate, 3α-hydroxy-chlormadinone acetate and 3β-hydroxy-chlormadinone acetate preferably as sole gestagen component and at least one oestrogen selected from the group consisting of ethinyl oestradiol, oestrone, oestriol and oestradiol preferably as sole oestrogen component.

As active substance combination for the production of a daily unit, use is preferably made in each case of a hormone combination of preferably 0.001 to 50 µg, particularly preferably 5 to 50 µg, very particularly preferably 5 to 30 µg of ethinyl oestradiol or preferably 0.01 to 60 mg, particularly preferably 0.5 to 50 mg, very particularly preferably 1 to 50 mg of oestrone or preferably 0.01 to 60 mg, particularly preferably 0.5 to 50 mg, very particularly preferably 1 to 50 mg of oestriol, or preferably 0.1 to 5 mg, particularly preferably 0.5 to 3 mg, very particularly preferably 1 to 2 mg of oestradiol as the preferably sole oestrogen component and of 1 to 10 mg, particularly preferably 2 to 5 mg, very particularly preferably 1 to 5 mg of chlormadinone acetate, 3α-hydroxy-chlormadinone acetate and/or 3β-hydroxy-chlormadinone acetate as the preferably sole gestagen component and optionally of conventional auxiliary materials.

In a particularly preferred embodiment of the present invention, the active substance combination used to produce a daily unit comprises a hormone combination consisting µ preferably of 0.001 to 50 µg, particularly preferably of 5 to 50 µg, very particularly preferably of 5 to 30 αg of ethinyl oestradiol or preferably of 0.1 to 5 mg, particularly preferably of 0.5 to 3 mg, very particularly preferably of 1 to 2 mg of oestradiol and of 1 to 10 mg, particularly preferably of 2 to 5 mg, very particularly preferably of 1 to 5 mg of chlormadinone acetate, 3β-hydroxy-chlormadinone acetate and optionally conventional auxiliary substances.

If, in addition to the treatment and/or prevention of melasma, it is also intended at the same time to provide satisfactory contraceptive protection or hormone replacement for women, a hormone combination consisting of in each case 15 µg, 20 µg or 30 µg of ethinyl oestradiol or 1 or 2 mg of oestradiol and in each case 1, 2, 3, 4 or 5 mg of chlormadinone acetate, 3α-hydroxy-chlormadinone acetate and/or 3β-hydroxy-chlormadinone acetate and optionally conventional auxiliary materials is preferably used to produce a daily unit.

In a particularly preferred embodiment of the present invention a hormonal active substance combination consisting of in each case 20 µg of ethinyl oestradiol and ≧2 mg of chlormadinone acetate, 3α-hydroxy-chlormadinone acetate and/or 3β-hydroxy-chlormadinone acetate is used per daily unit for the treatment and/or prevention of melasma and at the same time to achieve contraception.

If, in addition to the treatment of melasma according to the invention, it is also intended at the same time to carry out hormone replacement therapy, a daily unit preferably contains a hormonal active substance combination consisting of oestradiol and chlormadinone acetate, 3α-hydroxy-chlormadinone acetate and/or 3β-hydroxy-chlormadinone acetate. Preferably, such a medicament contains 0.5 to 3 mg, particularly preferably 1 to 2 mg of oestradiol and 1 to 10 mg, particularly preferably 1 to 5 mg of chlormadinone acetate, 3α-hydroxy-chlormadinone acetate and/or 3β-hydroxy-chlormadinone acetate and optionally conventional auxiliary materials.

Preferably, the hormone-containing daily units contain the same hormone combination in the same quantity with the same proportion of the gestagen or oestrogen component.

If the medicament used according to the invention contains a hormonal active substance combination as described above, it is provided in the form of at least 21 daily units containing one of the above-listed active substance combinations as hormone combination for uninterrupted administration, optionally followed by a 7- to 3-day interval in taking or by 7 to 3 hormone-free daily units for uninterrupted administration.

For the treatment or prevention of melasma and optionally simultaneous hormonal contraception or optionally simultaneous hormone replacement, the medicament may also be provided in the form of daily units in each case containing one of the above-listed hormone combinations as the active substance combination for uninterrupted administration also over several years, preferably for up to 2 years, particularly preferably for up to 1 year, optionally in combination with 7 to 3 hormone-free daily units for uninterrupted subsequent administration or followed by a 7 to 3 day interval in taking.

The medicament prepared according to the invention may, however, also be provided for treatment according to the invention in a dosage form with fewer than 365 daily units containing one of the above-listed hormonal active substance combinations, such as for example with 77 to 193 or 42 to 52 daily units containing one of the above-listed hormonal active substance combinations for uninterrupted oral administration, followed by an interval in taking of 7 to 3 days or by 7 to 3 hormone-free daily units for uninterrupted administration.

Where it is intended that the medicament be taken for up to 2 years, the above-stated dosage form, which comprises the daily units containing one of the above-listed active substance combinations and optionally the above-listed hormone-free daily units, may be made available in appropriate packaging.

In a further preferred embodiment of the present invention, the medicament used according to the invention may be provided in the form of 21 to 25 daily units containing one of the above-listed active substance combinations as the hormone combination for uninterrupted administration followed by 7 to 3 hormone-free daily units for subsequent uninterrupted administration or followed by an interval in taking of 3 to 7 days.

Accordingly, the medicament used according to the invention may also be present in a packaging with the above-listed number of hormone-containing and hormone-free daily units. In this case, the daily units containing one of the above-listed active substance combinations as the hormone combination and the hormone-free daily units are preferably packaged in blister packs. If the number of daily units present in a blister pack, preferably with an indication of the daily unit to be taken in each case, preferably corresponds to a female cycle of 28 days, a plurality of blister packs may be combined into a kit, for example comprising 1, 2, 3, 4, 5, 6, 7, 8, 9, 10, 11, 12, 13, 14 or 15 blister packs, each blister pack in each case containing a combination, as listed above, of hormone-containing and hormone-free daily units for uninterrupted administration.

In a particularly preferred embodiment of the present invention the medicament comprises quantitatively the same hormone combination in each daily unit containing one of the stated active substance combinations as hormone combination, said same hormone combination consisting of at least one oestrogen preferably selected from the group consisting of ethinyl oestradiol and oestradiol and at least one gestagen selected from the group consisting of chlormadinone acetate, 3α-hydroxy-chlormadinone acetate and 3β-hydroxy-chlormadinone acetate, the composition of the respective hormone combinations also not varying quantitatively.

The daily units, preferably present in the form of tablets, of the medicament according to the invention may be produced using conventional formulation methods known to a person skilled in the art.

EXAMPLES a) Production of the Medicament

Example 1

Composition

|  | Per tablet | Per batch |
|---|---|---|
| Ethinyl oestradiol | 0.020 mg | 0.0020 kg |
| Chlormadinone acetate | 2.000 mg | 0.2000 kg |
| Povidone K30 | 3.000 mg | 0.3000 kg |
| Lactose | 32.980 mg | 3.2980 kg |
| Maize starch | 12.000 mg | 1.2000 kg |
| Magnesium stearate | 0.500 mg | 0.0500 kg |
| Highly disperse silicon dioxide | 0.500 mg | 0.0500 kg |

Ethinyl oestradiol (EO) and povidone K30 (PVP) were dissolved in 600 ml of ethanol. Chlormadinone acetate (particle size 90%<50 µm), lactose and maize starch were mixed in a mixer/pelletiser (Diosna P25) for 5 mins and then moistened thoroughly and mixed with the ethanolic EO/PVP solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 5 mm punches into tablets with a weight of 50 mg.

The tablets were coated with a methylhydroxypropylcellulose-based coating of the following composition (coating mass 2 mg per tablet)

| Methylhydroxypropylcellulose 6 mPa · s, | 0.1351 kg |
|---|---|
| Polyethylene glycol 6000 | 0.0395 kg |
| Propylene glycol | 0.0054 kg |
| Purified water | 1.6200 kg |

In each case 24 tablets as the daily units containing the hormonal active substance combination and in each case 4 correspondingly composed, hormone-free tablets were packaged in a blister pack.

Example 2

Tablets of the following composition were produced in a manner similar to Example 1:

|  | Per tablet | Per batch |
|---|---|---|
| Ethinyl oestradiol | 0.030 mg | 0.0030 kg |
| Chlormadinone acetate | 2.000 mg | 0.2000 kg |
| Povidone K30 | 3.000 mg | 0.3000 kg |
| Lactose | 32.970 mg | 3.2970 kg |
| Maize starch | 12.000 mg | 1.2000 kg |
| Magnesium stearate | 0.500 mg | 0.0500 kg |
| Highly disperse silicon dioxide | 0.500 mg | 0.0500 kg |

In each case 21 tablets were packaged in a blister pack as daily units containing the hormonal active substance combination.

b) In Vitro Data

In a series of experiments, the influence of chlormadinone acetate (CMA) on the proliferation or pigment formation of human melanocytes was examined.

To this end, human melanocytes were cultured in each case in the corresponding culture medium, which in each case contained different quantities of ethinyl oestradiol (EO), chlormadinone acetate (CMA) or a combination thereof. The individual compositions are summarised below in Table 1.

TABLE 1

| Formulation # | CMA | EO |
|---|---|---|
| 1 | − | + |
| 2 | + | − |
| 3 | + | + |

After 9 days the human melanocytes were analysed in vitro. Cell growth and cell death were determined by cell counting by means of Typan blue staining and by commercial cell proliferation and apoptosis tests. Pigment formation was determined both by measuring the melanin concentration of the cells and by measuring tyrosinase, the key enzyme in pigment formation.

It was possible to demonstrate that, in the presence of 1 nM of ethinyl oestradiol (cf. Table 1, formulation #1) as the sole hormone in the culture medium, tyrosinase activity or the proliferation of human melanocytes is increased.

It was also possible to demonstrate that, in the presence of chlormadinone acetate (cf. Table 1, formulation #2) (100 nM) in the culture medium, the proliferation rate of human melanocytes is reduced by 50-70%.

In the case of human melanocyte cultures which were cultivated in the presence of a hormone combination (cf. Table 1, formulation #3) of ethinyl oestradiol and chlormadinone acetate, it was possible to observe a distinct reduction in the proliferation rate of the melanocytes in comparison with melanocyte cultures which were cultured solely in the presence of ethinyl oestradiol.

c) In Vivo Study

The action according to the invention of the medicament according to Example 2 was tested in a study involving 20,897 women, who took a hormonal active substance combination consisting of 30 µg of ethinyl oestradiol and 2 mg of chlormadinone acetate per daily unit for a duration of 4 menstrual cycles.

Melasma only occurred in 4 of the 20,897 women who took part in the study. This amounts to 0.019% of the participating women.

It was additionally possible to demonstrate that, in the case of participating women who already had melasma as the result of previously taking a hormonal active substance preparation containing a different hormone combination from the hormone combination according to the invention, such women were able to be cured by taking the medicament according to Example 2 or a distinct improvement of the hyperpigmentation of their facial skin could be achieved.

The invention claimed is:

1. A method for treatment or prevention of melasma in women, comprising administering to a women at least one gestagen selected from the group consisting of chlormadinone acetate, 3a-hydroxy-6-chloro-17α-acetoxy-4,6-pregnadien-20-one (3α-hydroxy-chlormadinone acetate) and 3β-hydroxy-6-chloro-17α-acetoxy-4,6-pregnadien-20-one (3β-hydroxy-chlormadinone acetate) as gestagen component and optionally at least one oestrogen selected from the group consisting of ethinyl oestradiol, oestrone, oestriol and oestradiol as oestrogen component.

2. The method according to claim 1, wherein the medicament is provided in the form of daily units.

3. The method according to claim 1, wherein a daily unit is produced by using as the only hormonal active substance a gestagen component selected from the group consisting of chlormadinone acetate, 3β-hydroxy-chlormadinone acetate and 3β-hydroxy-chlormadinone acetate.

4. The method according to claim 1, wherein the gestagen component is used in a quantity of from 1 to 10 mg.

5. The method according to claim 4, wherein a daily unit is produced by using 1, 2, 3, 4 or 5 mg of the gestagen component and optionally conventional auxiliary materials.

6. The method according to claim 4, wherein the medicament is provided in the form of at least 28 daily units containing the gestagen component as hormonal active substance for uninterrupted daily oral administration.

7. The method according to claim 3, wherein the medicament is provided in the form of 28, 56, 84, 112, 140, 168, 196, 224, 252, 280, 308, 336 or 364 daily units for uninterrupted daily oral administration.

8. The method according to claim 1, wherein the active substance combination used comprises a hormone combination consisting of at least one gestagen selected from the group consisting of chlormadinone acetate, 3α-hydroxy-6-chloro-17α-acetoxy-4,6-pregnadien-20-one (3α-hydroxy-chlormadinone acetate) and 3β-hydroxy-6-chloro-17α-acetoxy-4,6-pregnadien-20-one (3β-hydroxy-chlormadinone acetate) as the gestagen component and at least one oestrogen selected from the group consisting of ethinyl oestradiol, oestrone, oestriol and oestradiol as the oestrogen component.

9. The method according to claim 8, wherein a daily unit is produced by using a hormone combination consisting of 5 to 50 µg of ethinyl oestradiol, 0.5 to 3 mg of oestradiol, 0.5 to 50 mg of oestrone or 0.5 to 50 mg of oestriol and 1 to 5 mg of the gestagen component and optionally conventional auxiliary substances.

10. The method according to claim 8, wherein a daily unit is produced by using a hormone combination consisting of 5 to 30 pg of ethinyl oestradiol or 1 to 2 mg of oestradiol and 1 to 5 mg of the gestagen component and optionally conventional auxiliary substances.

11. The method according to claim 8, wherein a daily unit is produced by using a hormone combination consisting of in each case 15 µg, 20 µg or 30 µg of ethinyl oestradiol or in each case 1 or 2 mg of oestradiol as oestrogen component and in each case 1, 2, 3, 4 or 5 mg of the gestagen component and optionally conventional auxiliary substances.

12. The method according to claim 8, wherein for each a daily unit a hormone combination of in each case 20 µg of ethinyl oestradiol and 2, 3, 4 or 5 mg of the gestagen component is used.

13. The method according to claim 8, wherein the medicament is provided in the form of at least 21 daily units containing the hormone combination as active ingredient combination for uninterrupted administration optionally followed by a 7 to 3 day interval in taking or by 7 to 3 hormone-free daily units for uninterrupted administration.

14. The method according to claim 13, wherein the medicament is provided in the form of daily units containing one of the hormone combinations as active substance combination for uninterrupted administration over several years, preferably for up to 2 years, particularly preferably for up to 1 year, followed by 7 to 3 hormone-free daily units for uninterrupted administration or followed by an interval in taking of 3 to 7 days.

15. The method according to claim 13, wherein the medicament is provided in the form of 77 to 193 daily units containing one of the hormone combinations as active substance combination for uninterrupted administration followed by 7 to 3 hormone-free daily units for uninterrupted administration or followed by an interval in taking of 3 to 7 days.

16. The method according to claim 13, wherein the medicament is provided in the form of 42 to 52 daily units containing one of the hormone combinations as active substance combination for uninterrupted administration followed by 7 to 3 hormone-free daily units for uninterrupted administration or followed by an interval in taking of 3 to 7 days.

17. The method according to claim 13, wherein the medicament is provided in the form of 21 to 25 daily units containing one of the hormone combinations as active substance combination for uninterrupted administration followed by 7 to 3 hormone-free daily units for uninterrupted administration or followed by a 3 to 7 day interval in taking.

18. The method according to claim 17, wherein, in each daily unit containing one of the hormone combinations as active substance combination, the medicament comprises quantitatively the same combination of oestrogen component and gestagen component.

19. The method according to claim 1 wherein the proliferation of human melanocytes is inhibited.

20. The method according to claim 1 wherein the melanin content in human melanocytes is reduced.

21. The method according to claim 4 wherein the gestagen component is used in a quantity of from 2 to 5 mg.

* * * * *